(12) United States Patent
Nelson

(10) Patent No.: US 10,067,238 B2
(45) Date of Patent: Sep. 4, 2018

(54) METHOD AND APPARATUS FOR ION BEAM BRAGG PEAK MEASUREMENT

(71) Applicant: Brett Nelson, Scotts Valley, CA (US)

(72) Inventor: Brett Nelson, Scotts Valley, CA (US)

( * ) Notice: Subject to any disclaimer, the term of this patent is extended or adjusted under 35 U.S.C. 154(b) by 550 days.

(21) Appl. No.: 14/459,137

(22) Filed: Aug. 13, 2014

(65) Prior Publication Data
US 2016/0049216 A1 Feb. 18, 2016
US 2017/0322316 A9 Nov. 9, 2017

Related U.S. Application Data

(60) Provisional application No. 61/959,050, filed on Aug. 13, 2013.

(51) Int. Cl.
*A61N 5/10* (2006.01)
*G01T 1/02* (2006.01)
*G01T 1/29* (2006.01)

(52) U.S. Cl.
CPC ............ *G01T 1/023* (2013.01); *A61N 5/1075* (2013.01); *G01T 1/29* (2013.01); *A61N 2005/1076* (2013.01); *A61N 2005/1087* (2013.01); *A61N 2005/1095* (2013.01)

(58) Field of Classification Search
CPC .......... A61N 2005/1095; A61N 5/1048; A61N 2005/1087; H05H 2007/004
See application file for complete search history.

(56) References Cited

U.S. PATENT DOCUMENTS

| | | | |
|---|---|---|---|
| 8,674,318 B2* | 3/2014 | Iwata | A61N 5/10 250/396 ML |
| 2011/0240874 A1* | 10/2011 | Iwata | G21K 1/043 250/396 ML |

OTHER PUBLICATIONS

"Logos Chevron Wedge 140" data sheet published Sep. 17, 2013, available at http://www.logosvisionsystem.com/downloads.html.*
XRV2000 Data sheet, published at least by Jul. 29, 2014, available at http://www.logosvisionsystem.com/downloads.html.*
"Multi-layer energy filter for realizing conformal irradiation in charged particle therapy", Med. Phys. 27 (2), Feb. 2000. p. 368-373 to Sakae et al.*

* cited by examiner

*Primary Examiner* — Kenneth J Malkowski

(57) ABSTRACT

A system and method for recording in real-time the duration, position, and energy of ion beams as delivered by a proton or heavy ion cancer treatment system for the purpose of calibrating the radiological system and verifying the treatment plans for various lesions. The energy of the ion beam is calculated from the beam ion depth penetration through a phantom as recorded on a two-dimensional scintillator surface which is viewed by a sensitive visible-light camera mounted in a darkened enclosure. The energy of the beam is degraded by a multi-step dual-slope chevron wedge phantom which creates, at a minimum, two bright spots in the camera's field of view. The distance between the centers of these two spots along with the dimensions and density of the multi-step dual-slope chevron wedge are used to calculate the Bragg Peak penetration depth of the ion beam.

9 Claims, 5 Drawing Sheets

METHOD AND APPARATUS FOR ION BEAM BRAGG PEAK MEASUREMENT

Provisional Patent Filed: Aug. 13, 2013 Ser. No. 61/959,050

REFERENCES CITED

| | | | |
|---|---|---|---|
| 6,639,234 | October, 2003 | Badura, et al. | 250/492.3, 505.1 |
| 6,670,618 | December, 2003 | Hartmann, et al. | 250/492.3 |
| 7,636,419 | February, 2006 | Nelson | 378/207 |
| 7,714,309 | May, 2010 | Mackie, et al. | 250/492.3 |
| 8,426,824 | April, 2013 | Jongen, et al. | 250/370.01 |

OTHER PUBLICATIONS

I. Rinaldi, et al., "Experimental characterization of a prototype detector system for carbon ion radiography and tomography," Phys. Med. Biol. 58 (2013) 413-427

FIELD OF THE INVENTION

This invention relates to the automated electronic measurement of ion beam depth penetration for the purpose of validating the performance of proton and heavy ion beam therapy systems.

BACKGROUND OF THE INVENTION

Proton and heavy ion beam radiation therapy is a cancer treatment modality that is growing in availability as an alternative to traditional radiosurgery using x-rays and gamma rays. In this modality the ion beam is delivered in a two-dimensional pattern over the surface of the patient on a vector directed towards the lesion. The depth of penetration of the ions is related to the energy of the beam and is commonly called the Bragg Peak. Knowing and being able to control the depth of penetration therefore becomes vital in assuring that the maximum radiation will be delivered correctly, not before or after the tumor site, along the ion vector path.

A simple and efficient form of Bragg Peak penetration depth measurement employs a wedge-shaped object comprised of plastic or another material with a density comparable to water (tissue). This wedge is then placed in the path of the ion beam and positioned in front of a sensing apparatus that uses ion chambers, scintillator, or film to record the intensity of the ionizing radiation reaching the apparatus. The apparatus will record a maximum stimulus at the linear position along the wedge where the wedge thickness corresponds to the ion beam's characteristic energy.

The wedge technique has been used extensively since William Henry Bragg first discovered the relationship between ion beam energy and depth of penetration, reportedly in 1903, and published in 1904 (Radiother Oncol. 2004 Dec; 73 (3):265-8.) http://www.ncbi.nlm.nih.gov/pubmed/15588869). Since the beam energies present in modern ion beam delivery systems can exceed 300 MeV, the size of wedge necessary for capturing a range of beam energies can exceed 300 millimeters; thus requiring a large corresponding size for film, ion chamber, or scintillator detection systems. As the detector size increases for each of these technologies, so does the cost of the detector.

BACKGROUND OF THE INVENTION

Objects and Advantages

The present invention described is unique in that the wedge is segmented into a series of adjacent steps. In this way, the wedge's linear design can be folded into a smaller two-dimensional footprint thus reducing the size and cost of the detector.

In addition, this invention provides a mirror image of each slope in a given step so that two Bragg peak measurements can be made simultaneously. These dual measurements are then averaged together to increase the overall precision of the captured data. Another benefit of having multiple raw data points, is that the style of image processing and machine vision metrology algorithms used to automate the measurement process can be simplified.

The advantages of this multi-stepped dual-slope chevron wedge over the traditional simple wedge are a smaller more economical detector size and higher quality measurements performed quickly via a process that can be readily automated with a computer and appropriate software.

The present invention can be used in conjunction with film and two-dimensional arrays of ion chamber sensing devices, but the preferred embodiment is with scintillator screens that are located in the field of view of a sensitive CCD digital camera. Low-cost screens made with coatings of gadolinium oxysulfide (GOS) scintillator phosphors are suitable for providing good contrast between the various regions of the ion beam Bragg peak as produced by the stepped dual-slope chevron structure. The two-dimensional image from the camera can then be readily analyzed by image processing software to generate the penetration depth measurements.

The use of a single detector rather than multiple ion chambers or semiconductor radiation detectors as discussed in the cited prior art simplifies the design of the invention, lowering its relative cost of manufacture.

SUMMARY OF THE INVENTION

The present invention features a multi-stepped dual-slope chevron wedge structure of material with known density and dimensions resting on the backside of a surface coated with scintillator phosphor that is capable of fluorescing with visible light when struck with ionizing radiation. The frontside which has the scintillator material faces a CCD camera in a darkened enclosure.

When the ion beam within a specific energy range strikes the multi-stepped dual-slope chevron wedge, at least two bright spots will be generated on the scintillator that correspond to the penetration depth of the beam. The camera then sends the image of the scintillator containing these two spots to the computer which determines the positions of peak intensity. These positions along with the water equivalent dimensions of the chevron wedge are then used to calculate the Bragg Peak penetration depth. The multi-stepped dual-slope chevron wedge phantom, enclosure, camera, and computer comprise the apparatus of the invention.

There are many methods by which the apparatus may be used to make Bragg Peak penetration depth measurements. The preferred embodiment described here is a software program that continually monitors any beam activity on the scintillator image during beam delivery. As each beam is detected and measured, the penetration depth data is recorded in computer memory. In addition, the brightness and duration of the beam may also be recorded. In this way, an entire range of ion beam energies and dosimetric information used in a diagnostic treatment plan can be captured in real-time and studied for accuracy.

BRIEF DESCRIPTION OF THE DRAWINGS

While the specification concludes with claims particularly pointing out and distinctly claiming the present invention, objects and advantages of the invention can be more readily ascertained from the following description of a preferred embodiment when used in conjunction with the accompanying drawings in which:

DETAILED DESCRIPTION OF THE INVENTION

Figure 1:
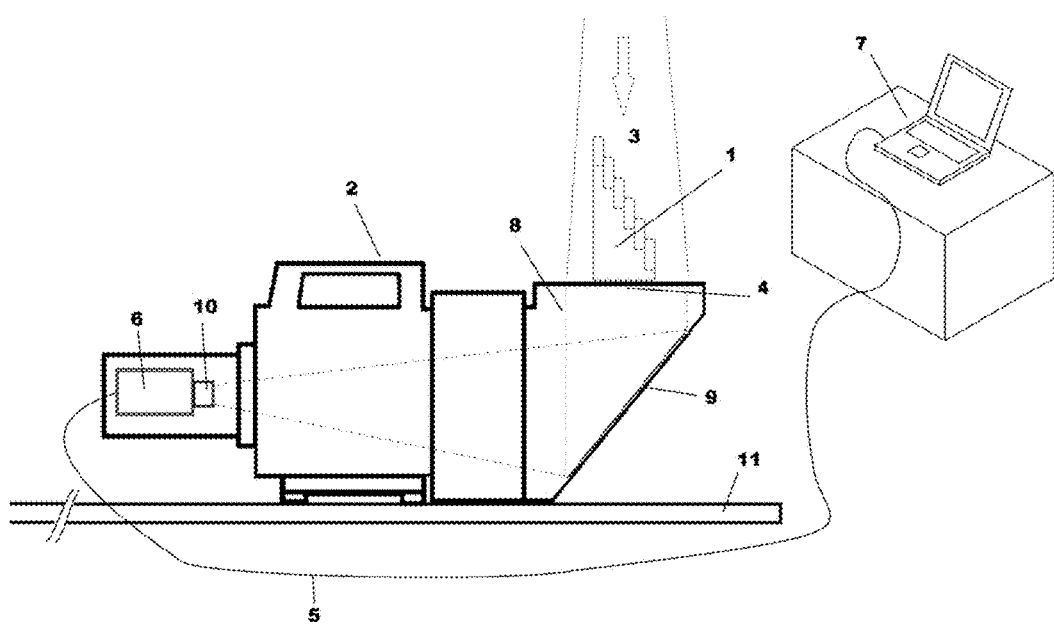
FIG. 1 is a side view of the multi-step dual-slope chevron wedge phantom mounted above the dosimeter detector. The dosimeter detector is connected to the computer which analyzes the radiographic images produced when the ion beam strikes the phantom and dosimeter detector.

Referring now to FIGS. 1, 2, 3, 4, and 5, a multi-stepped dual-slope chevron wedge phantom 1 of water equivalent dimensions is mounted above a dosimeter detector module 2 capable of producing a two dimensional image of the ion beam 3 projected vertically down through the phantom striking the active surface 4 of the dosimeter detector 2. The ion beam may consist of protons or heavy ions such as carbon that have energies in the range of 50 to 500 MeV as generated by a cyclotron or synchrotron and then steered towards the phantom via electromagnetic fields and/or a gantry delivery system. The ions 3 that complete their journey through the phantom 1 deposit their remaining energy on the active surface 4 of the dosimeter detector 2 forming two to four characteristic bright regions which correspond to the Bragg Peak penetration depth of the ions in water. A cable 5 transfers images from the dosimeter detector camera 6 to the computer 7 which interprets the images into a three-dimensional dose pattern. The dosimeter detector 2 is typically placed at the end of the patient positioning couch 11 located near the ion beam 3 source in the ion beam therapy treatment room. The computer 7 is usually located in the control room which is typically separated from the treatment room by a distance of 10 to 30 meters.

The ion beam 3 passes through the multi-step dual-slope chevron wedge 1 entering the dosimeter detector 2 fluorescing the interior scintillator coating 4 forming an ion beam radiograph of the multi-step dual-slope chevron wedge phantom 1 vertical profile. Scintillating phosphors made up of gadolinium oxysulfides (GOS) doped with the lanthanide elements have been found to work well with proton beam energies up to 230 MeV. The visible light photons 8 from the ion beam 3 radiograph are reflected off the mirror 9 to the C-mount lens 10 attached to camera 6 that has a threshold of sensitivity of 0.01 lux or better. The camera 6 and C-mount lens 10 are adjusted so that maximum amount of scintillator 4 is visible and in focus. The camera 6 is positioned along the central axis of the detector 2 enclosure so that the center of the scintillator 4 is at the center of the field of view. Scaling factors that convert the image pixels into horizontal and vertical distances in millimeters are determined through calibration techniques using the camera and optics. The cable 5 transfers a stream of scintillator 4 images from camera 6 to the dosimeter computer 7. A point is chosen on the scintillator 4 to serve as the origin for the Cartesian coordinate system used in analyzing the scintillator 4 images and calculating the XY values for regions on the ion beam radiograph using the camera scaling factors.

Figure 2:
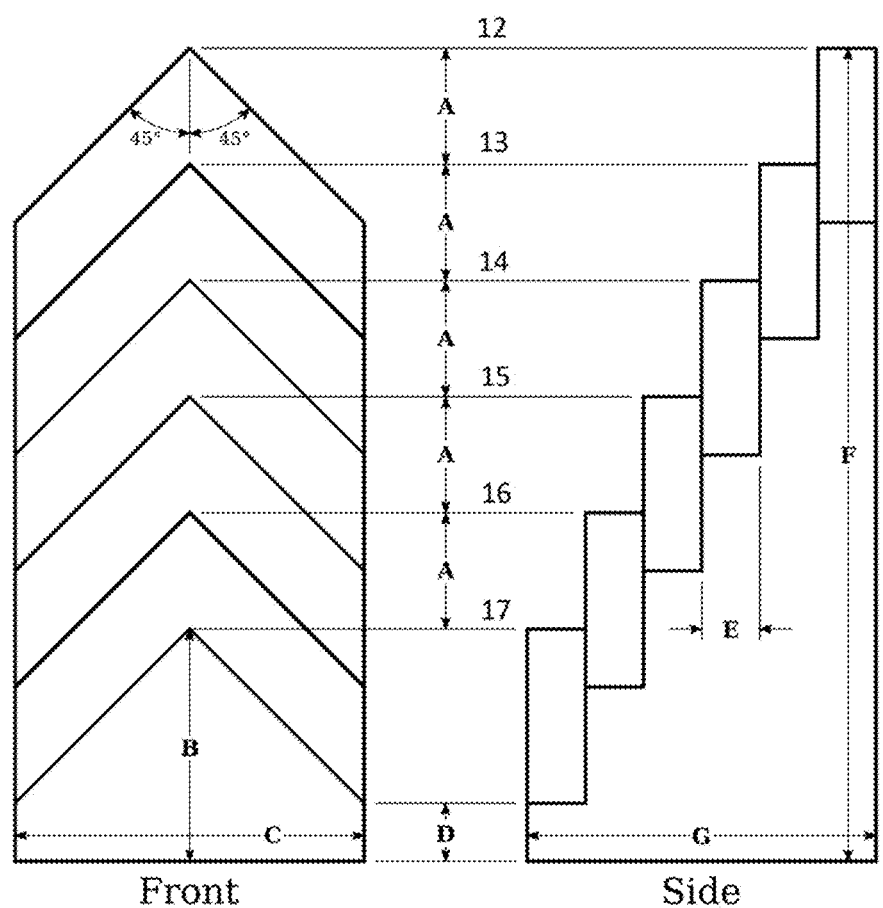
FIG. 2 is a front and side view of the multi-step dual-slope chevron wedge annotated with sample water equivalent dimensions. These dimensions will be needed to calculate the Bragg Peak penetration depth.

Referring now to FIG. 2 showing the Front and Side views of the dual-slope chevron wedge preferred embodiment which has 6 adjacent chevron-shaped steps 12 13 14 15 16 17 with each step having a decreasing height and a constant thickness of E millimeters. Experimentation has shown that the minimum value of E should be about 10 mm in order to minimize the effects of ion scattering on the resulting radiograph image. The slope height range of D to F establishes the minimum and maximum Bragg Peak penetration depths measureable by the phantom. For reference, proton beams with energies near 100 MeV have an approximate penetration of 100 mm so it is reasonable that there could be several embodiments of the phantom, each one with a different height range designed for a particular range of ion energies. The dual 45 degree angle at the top of each chevron 12 13 14 15 16 17 serves to simplify Bragg Peak calculations because each millimeter travelled horizontally from the chevron peak along the slope corresponds to a vertical drop of one millimeter. The entire phantom 1 footprint of C x G millimeters should be illuminated by the ion beam 3 in order for the camera 6 to capture the bright regions on the scintillator associated with the ion beam's 3 characteristic Bragg Peak penetration depth.

The dimensions shown in FIG. 2 are given as if the phantom 1 consisted of a substance the same density as liquid water. In reality, the phantom 1 would be fabricated using plastic or ceramic, and the physical dimensions would need to be scaled to their water equivalent dimensions using the ratio of the density of the material compared to water when exposed to the particular kind of ion beam. If the phantom 1 is composed of acrylic plastic (PMMA) and the beam ions are protons, then this ratio is approximately 1.14.

Figure 3:
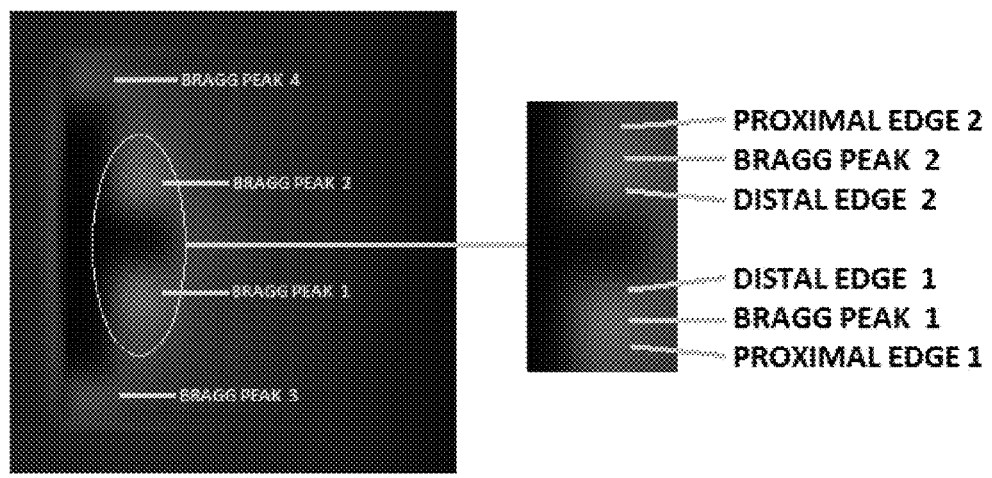
FIG. 3 is a sample proton beam radiograph of the multi-step chevron wedge as imaged by the scintillator and seen by the camera. The two dominant Bragg Peak regions are magnified and annotated.

Referring now to FIG. 3 showing the ion beam radiograph, the four bright regions correspond to the Bragg Peak penetration depths of the ion beam on the two tallest chevrons 12 13 of the phantom 1. The regions located on the next tallest chevron 13 contain the most complete Bragg Peak grayscale gradient and are labelled Bragg Peak 1 and Bragg Peak 2. The side of the region that has the sharpest transition to black is called the distal edge and the opposite side is the proximal edge as labelled in the magnified view of the two regions. The black region between the distal edges of the two bright spots represents those ions that had insufficient energy to make the complete traversal through the tallest part of the chevron 13 to the scintillator 4 surface under the phantom 1. Most of the tallest portions of chevron 12 are dark because they represent path lengths that exceeded the penetration depth of the ion beam 3 leaving little energy to impart to the scintillator 4.

Figure 4:
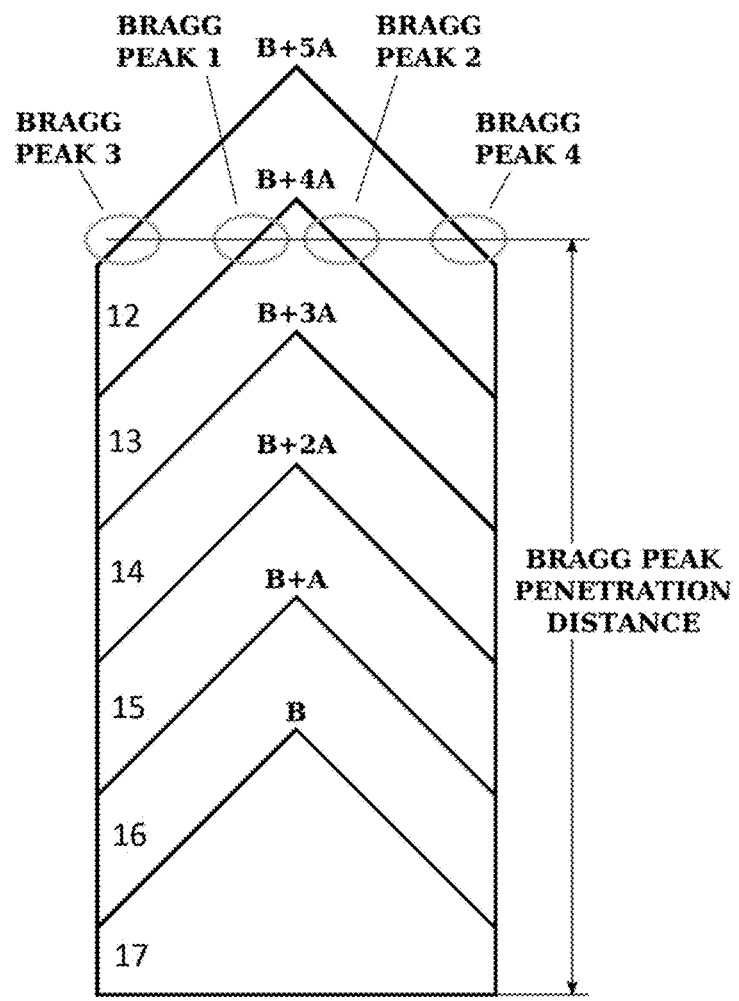
FIG. 4 represents the Bragg Peak penetration depth as viewed from the front of the multi-step dual-slope chevron wedge phantom. The relative vertical entry position associated with the four bright Bragg Peak regions from FIG. 3 are highlighted along with their distance from the base of the phantom.

Referring now to FIG. 4 showing the front view of two chevrons 12 13, it can be seen that the Bragg Peak penetration depth is constant for the particular energy of the ion beam 3 in the phantom 1 regardless of whether the path travelled started on the tallest chevron 12 or the next tallest 13. The ions that travelled a longer distance in the phantom than the penetration depth deposited more of their energy in the phantom 1 and less on the scintillator 4 surface. These areas of the scintillator 4 are darker compared to shorter ion paths.

Figure 5:
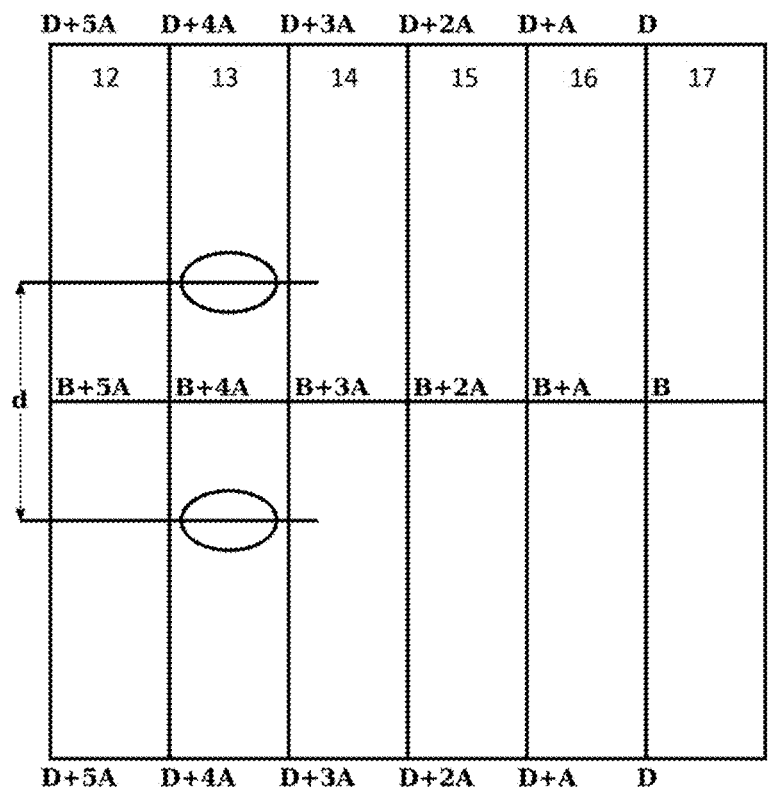
FIG. 5 shows a diagrammatic representation of the proton beam radiograph and the location of the two major Bragg Peak regions with the line of maximum brightness of each region highlighted. The dual-slope chevron wedge phantom dimensions from FIG. 2 are also identified. The equation used for calculating the Bragg Peak penetration depth is shown under the diagram.

Referring now to FIG. 5, the positions of the main two white regions of the ion beam radiograph on the second tallest chevron 13 are superimposed on a diagram of the phantom 1 shown from a vertical point of view. The water equivalent height dimensions from FIG. 2 are included as annotations on each chevron 12 13 14 15 16 17 at the beginning and end of each slope. The Bragg Peak regions are located along the two slopes of chevron 13 and therefore must be at a vertical height less than the peak value B+4A and greater than the side value of D+4A. Since the slopes are both at a 45 degree angle the depth can be calculated as the peak height B+4A minus half the distance d between the points of maximum grayscale intensity on the chevron 13.

The use of the multi-stepped dual-slope chevron wedge phantom 1 enables the dosimeter detector 2 and computer 7 to measure the energy of ion beam 3 that illuminates the entire phantom footprint. The brightest image regions shown in FIG. 3 and diagrammed in FIG. 5 can be determined with histogram image processing. Once the location of the two regions with the brightest pixels on the captured image are determined, the pixel distance between these two regions can be converted into millimeters through the image scaling parameters based on the field of view and focal length established while calibrating the camera 6 and lens 10. This distance along with the water equivalent dimensions of the phantom 1 can then be used with the equation of FIG. 5 to calculate the Bragg Peak penetration depth and hence the ion beam 3 energy.

Diagnostic treatment plans on the ion therapy system can then be created to deliver a number of beams 3 of different energies directed at the phantom. The computer 7 can be readily programmed to detect beam activity on the scintillator 4 image, and if present, save the beam image and the number of camera frames that the beam persists into memory in real-time as the treatment plan is delivered.

Once captured, the sequence of beam energies can be measured from the radiographic scintillator 4 images and the beam energy measurements can be archived to a disk file. Once saved to disk in a Comma Separated Value format or as a DICOM file, the measurements can be compared by the operator to the treatment plan beam energies identifying any differences between the intended and measured penetration depths.

While the invention has been particularly shown and described with reference to a preferred embodiment thereof, it will be understood by those skilled in the art that various changes in form and details may be made without departing from the spirit and scope of the invention.

What is claimed is:

1. A dosimeter apparatus comprising:
   an ion beam source;
   a two-dimensional sensing detector for providing a proportional response to input energy; and
   a multi-stepped dual-slope chevron wedge structure of known dimensions and density placed between the ion beam source and the two-dimensional sensing detector, the wedge structure being configured so as to produce a two-dimensional radiation pattern comprising at least one pair of Bragg peaks, a distance between the pair of Bragg peaks being indicative of ion beam energy after passing through the web structure.

2. A dosimeter apparatus according to claim 1, comprising:
   a computer,
   a high sensitivity camera, and
   a two-dimensional scintillator configured for detecting and measuring the position and brightness of the ion beam passing through the multi-stepped dual-slope chevron wedge in real time.

3. A dosimeter apparatus according to claim 1, comprising:
   a computer and
   a two-dimensional array of ion chambers configured for detecting and measuring the position and brightness of the ion beam passing through the multi-stepped dual-slope chevron wedge in real-time.

4. A dosimeter apparatus according to claim 1, comprising:
   a computer,
   a film camera and
   a scanner configured for detecting and measuring the position and brightness of the ion beam passing through the multi-stepped dual-slope chevron wedge.

5. A dosimeter apparatus according to claim 1, comprising electronics configured to electronically measure the Bragg Peak depth penetration of ion beams using two-dimensional images produced by the two-dimensional sensing detector.

6. A dosimeter apparatus according to claim 1, comprising electronics configured to electronically measure the position and duration of pulsed ion beams.

7. A dosimeter apparatus according to claim 1 wherein the multi-stepped dual-slope chevron wedge is made of a substance has water equivalent density.

8. A dosimeter apparatus according to claim 1 wherein wedge slopes on a given step of the wedge structure overlaps a vertical height range of slopes on an adjacent step such that up to four Bragg Peak positions may be measured at once.

9. A dosimeter apparatus according to claim 1 wherein a number of wedge steps and an overall maximum height of the wedge structure are arranged in accordance with a given of range of ion beam energy.

* * * * *